(12) United States Patent
Toth

(10) Patent No.: US 6,359,958 B2
(45) Date of Patent: Mar. 19, 2002

(54) METHODS AND APPARATUS FOR Z-POSITIONING AN X-RAY BEAM ON A MULTI-SLICE DETECTOR

(75) Inventor: Thomas L. Toth, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/746,456

(22) Filed: Dec. 21, 2000

Related U.S. Application Data

(63) Continuation-in-part of application No. 09/384,169, filed on Aug. 27, 1999.

(51) Int. Cl.$^7$ .................................................. A61B 6/00
(52) U.S. Cl. ......................................... 378/19; 378/205
(58) Field of Search ............................. 378/4, 19, 147, 378/150, 151, 205, 11, 8, 5

(56) References Cited

U.S. PATENT DOCUMENTS 6,056,437 A * 5/2000 Toth ........................... 378/205

FOREIGN PATENT DOCUMENTS

DE 19650528 A1 * 6/1997

* cited by examiner

Primary Examiner—David P. Porta
Assistant Examiner—Pamela R. Hobden
(74) Attorney, Agent, or Firm—Quarles & Brady, LLP; Christian G. Cabou

(57) ABSTRACT

In one embodiment, the present invention is a method for positioning an x-ray beam on a multi-slice detector array of an imaging system in which the detector array has rows of detector elements and is configured to detect x-rays in slices along a z-axis. The method includes steps of comparing data signals representative of x-ray intensity received from different rows of detector elements in first and second element subsets where the first and second subsets are located at opposite ends of the detector array and positioning the x-ray beam in accordance with a result of the comparisons.

22 Claims, 6 Drawing Sheets

METHODS AND APPARATUS FOR Z-POSITIONING AN X-RAY BEAM ON A MULTI-SLICE DETECTOR

CROSS-REFERENCE TO RELATED APPLICATIONS

This is a continuation in part of U.S. patent application Ser. No. 09/384,169 that was filed on Aug. 27, 1999, that is entitled "Methods and Apparatus for Positioning a CT Imaging X-ray Beam" and that is commonly owned by the present applicant.

STATEMENT REGARDING FEDERALLY SPONSORED RESEARCH OR DEVELOPMENT

Not applicable.

BACKGROUND OF THE INVENTION

This invention relates generally to computed tomography (CT) imaging and, more particularly, to methods and apparatus for positioning an X-ray beam in a multi-slice CT imaging system.

In at least one known computed tomography (CT) imaging system configuration, an X-ray source projects a fan-shaped beam which is collimated to lie within an X-Y plane of a Cartesian coordinate system and generally referred to as the "imaging plane". The X-ray beam attenuated by the object impinges upon an array of radiation detectors having first and second array ends. The intensity of the attenuated beam radiation received at the detector array is dependent upon the attenuation of the X-ray beam by the object. Each detector element of the array produces a separate electrical signal that is a measurement of the beam attenuation at the detector location. The attenuation measurements from all the detectors are acquired to produce a transmission profile.

In known third generation CT systems, the X-ray source and the detector array are rotated with a gantry within the imaging plane and around the object to be imaged so that the angle at which the X-ray beam intersects the object constantly changes. A group of X-ray attenuation measurement, i.e., projection data, from the detector array at one gantry angle is referred to as a "view". A "scan" of the object comprises a set of views made at different gantry angles, or view angles, during one revolution of the X-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In a multi-slice system including two or more rows of detector elements extending within the x-y plane between the first and second array ends, movement of an X-ray beam penumbra over detector elements having dissimilar response functions can cause signal changes resulting in image artifacts. Opening system collimation to keep detector elements in the X-ray beam umbra can prevent artifacts but increases patient dosage. Known CT imaging systems utilize a closed-loop z-axis tracking system to position the X-ray beam relative to a detector array. It would be desirable to provide a closed-loop system that operated during patient scanning to maintain the X-ray beam penumbra in the Z-axis at a position relative to a detector array row edge to minimize patient dosage, but far enough away from the edge to reduce artifacts.

One solution has been to, during data acquisition, dynamically track the Z-axis position of the penumbra and umbra with respect to array rows at a single end of the detector array and then adjusts the X-ray beam to maintain the relative position of the beam with respect to the rows. While this solution has managed to reduce artifacts and radiation during acquisition, this solution still has at least one important shortcoming that has hampered effectiveness. Specifically, this solution is based on the assumption that the entire X-ray beam moves identically as a function of beam fan angle. In other words, this solution assumes that the Z-axis locations of the penumbra and umbra at the single tracking end is identical to the Z-axis locations at the array end opposite the tracking end and is also identical at every point between the first and second array ends.

This assumption, while valuable, is not entirely accurate. As known in the art, twisting movements referred to generally as dynamic skew that occur during gantry rotation cause the X-ray beam to move differently in Z as a function of the beam fan angle. The disparate movement in Z has been shown to cause positioning errors of up to 0.3 mm on the detector array at isocenter even where tracking and dynamic beam adjustments maintain the relative position of the beam at the tracking end. This dynamic skew error prohibits virtually any penumbra from being used for data acquisition without the risk of generating artifacts and hence restricts ability to minimize dose reduction.

U.S. Pat. No. 5,299,250 entitled "Computer Tomography Apparatus With Compensation For Focus Migration By Adjustment Of Diaphragm Position" which issued on Mar. 29, 1994 describes one system wherein detectors at opposite ends of a detector array are used to identify Z-axis beam position at opposite ends of the array. Thereafter a collimator configuration is modified to maintain relative beam-detector position. While describing an advantageous solution to the dynamic skew problem, this patent fails to teach or suggest an optimal method or apparatus for determining beam location with respect to the detector at the tracking ends, how the two Z-axis positions are combined to adjust beam position and how the beam is controlled when one of the Z-axis detectors is blocked.

BRIEF SUMMARY OF THE INVENTION

There is therefore provided, in one embodiment, a method for positioning an X-ray beam on a multi-slice detector array of an imaging system in which the detector array has rows of detector elements and is configured to detect X-rays in slices along a Z-axis. The method includes the steps of comparing data signals representative of X-ray intensities received from a first detector subset in each row of a detector row subset to generate a first position command, the first detector subset located proximate a first array end, comparing data signals representative of X-ray intensities received from a second detector subset in each row of the detector row subset to generate a second position command, the second detector subset located proximate a second array end opposite the first array end and positioning the X-ray beam in accordance with a result of the comparisons.

The above described embodiment and systems performing this method periodically adjust the X-ray beam position to maintain the beam penumbra at a minimal distance from the detector array edge, so that patient dosage is minimized and imaging artifacts are reduced.

DETAILED DESCRIPTION OF THE INVETION

A. First Embodiment

This first embodiment, referred to as a single Z-position embodiment, describes several embodiments of a system that tracks beam-detector position at a single fan beam position and adjusts beam position as a function thereof.

Figure 1:
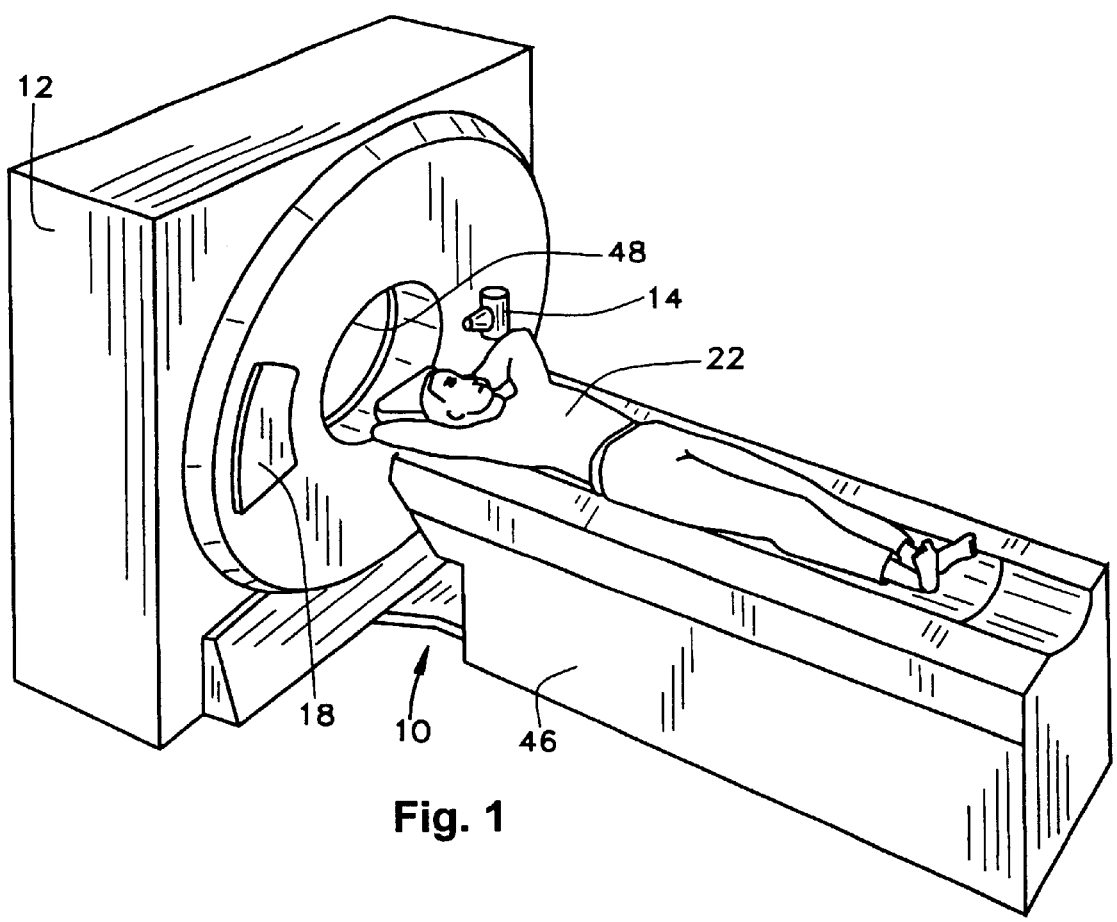
FIG. 1 is a pictorial view of a CT imaging system.
Figure 2:
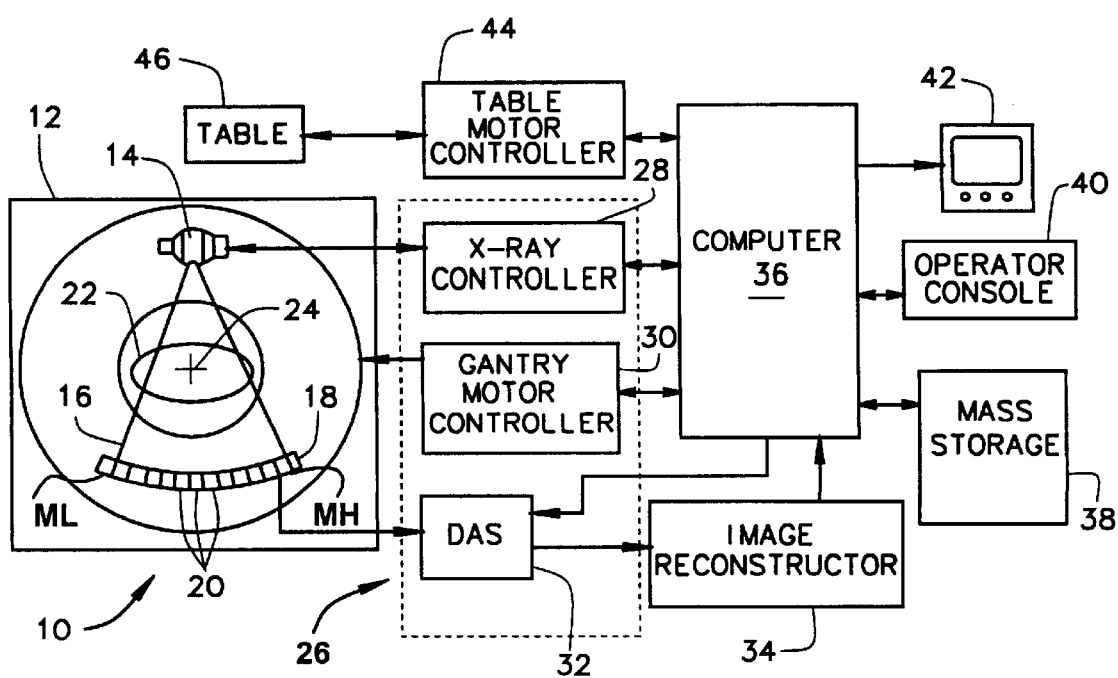
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an X-ray source 14 that projects a beam of X-rays 16 toward a detector array 18 on the opposite side of gantry 12. Detector array 18 is formed by detector elements 20 that together sense the projected X-rays that pass through an object 22, for example a medical patient. Each detector element 20 produces an electrical signal that represents the intensity of an impinging X-ray beam and hence the attenuation of the beam as it passes through patient 22. During a scan to acquire X-ray projection data, gantry 12 and the components mounted thereon rotate about a center of rotation or isocenter 24.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36 that stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

Figure 3:
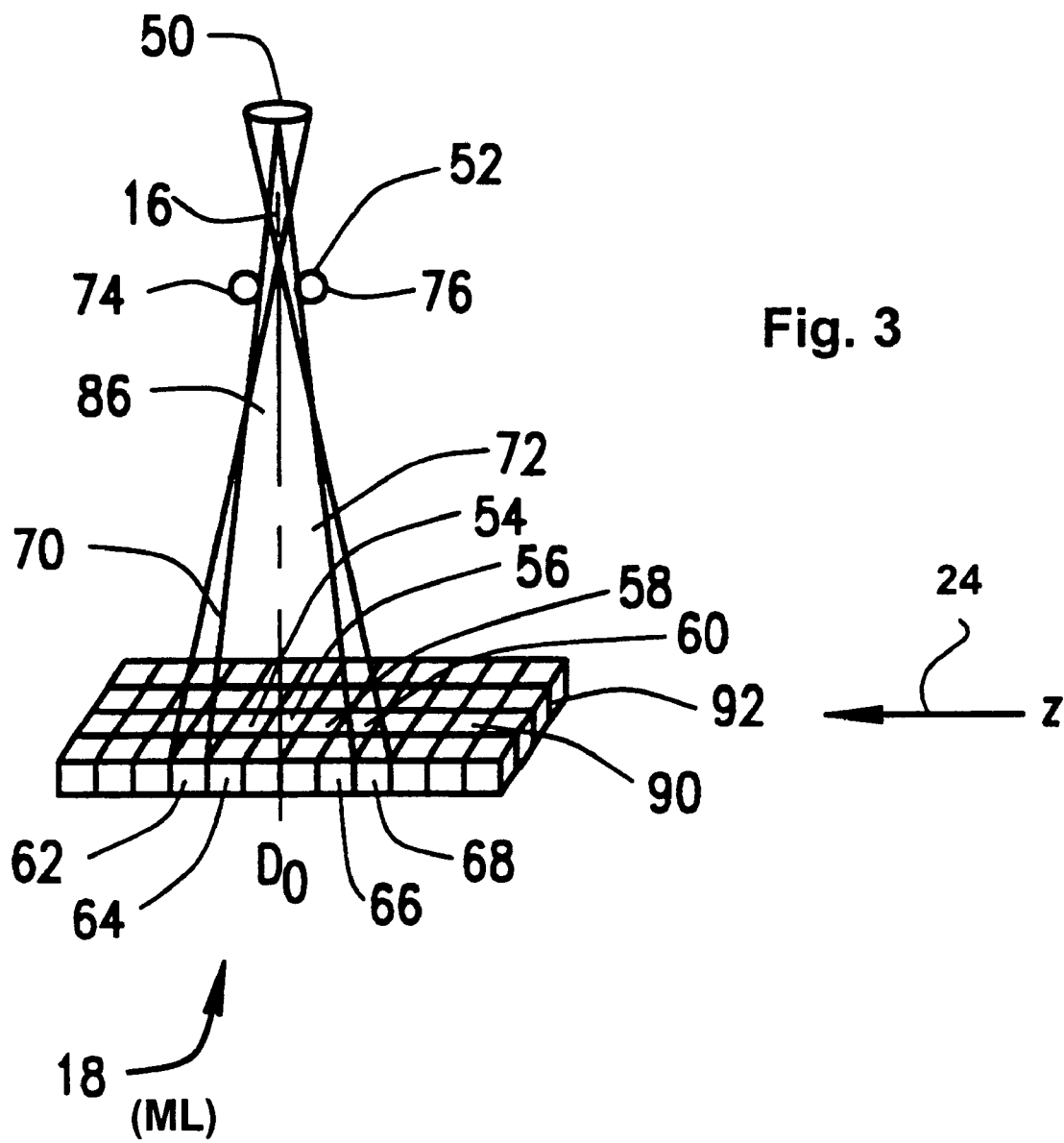
FIG. 3 is a schematic view of a portion of the CT imaging system shown in FIG. 1 showing an embodiment of a z-axis position system of the present invention.

In one embodiment, and as shown in FIG. 3, X-ray beam 16 emanates from a focal spot 50 of X-ray source 14 (FIG. 2). X-ray beam 16 is collimated by collimator 52, and collimated beam 16 is projected toward detector array 18. Detector array 18 is fabricated in a multi-slice configuration and includes detector element rows 54, 56, 58 and 60 for projection data collection. A plane 86, generally referred to as the "fan beam plane", contains the centerline of focal spot 50 and the centerline of beam 16. Fan beam plane 86 is illustrated in FIG. 3 as being aligned with a centerline $D_o$ of detector array 18, although fan beam plane 86 will not always be so aligned. Detector element rows 62, 64, 66 and 68 serve as z-position detectors for determining a z-axis position of X-ray beam 16. In one embodiment, detector rows 62, 64, 66 and 68 are rows of detector array 18. Outer rows 62 and 68 are selected to be at least substantially within penumbra 70 of beam 16. Inner rows 64 and 66 are selected to be at least substantially within or at least sufficiently within so that outer row 62 and 68 signal intensities depend on an X-ray beam position and inner row 64 and 66 signal intensities provide references against which outer row signals are compared. In one embodiment, collimator 52 includes tapered cams 74 and 76. (Where it is stated herein that a cam "has a taper," it is not intended to exclude cams having a taper of zero unless otherwise stated.) X-ray controller 28 controls positioning of cams 74 and 76. Each cam can be independently positioned to alter position and width of X-ray umbra 72 relative to an edge (not shown) of detector array 18.

Figure 4:
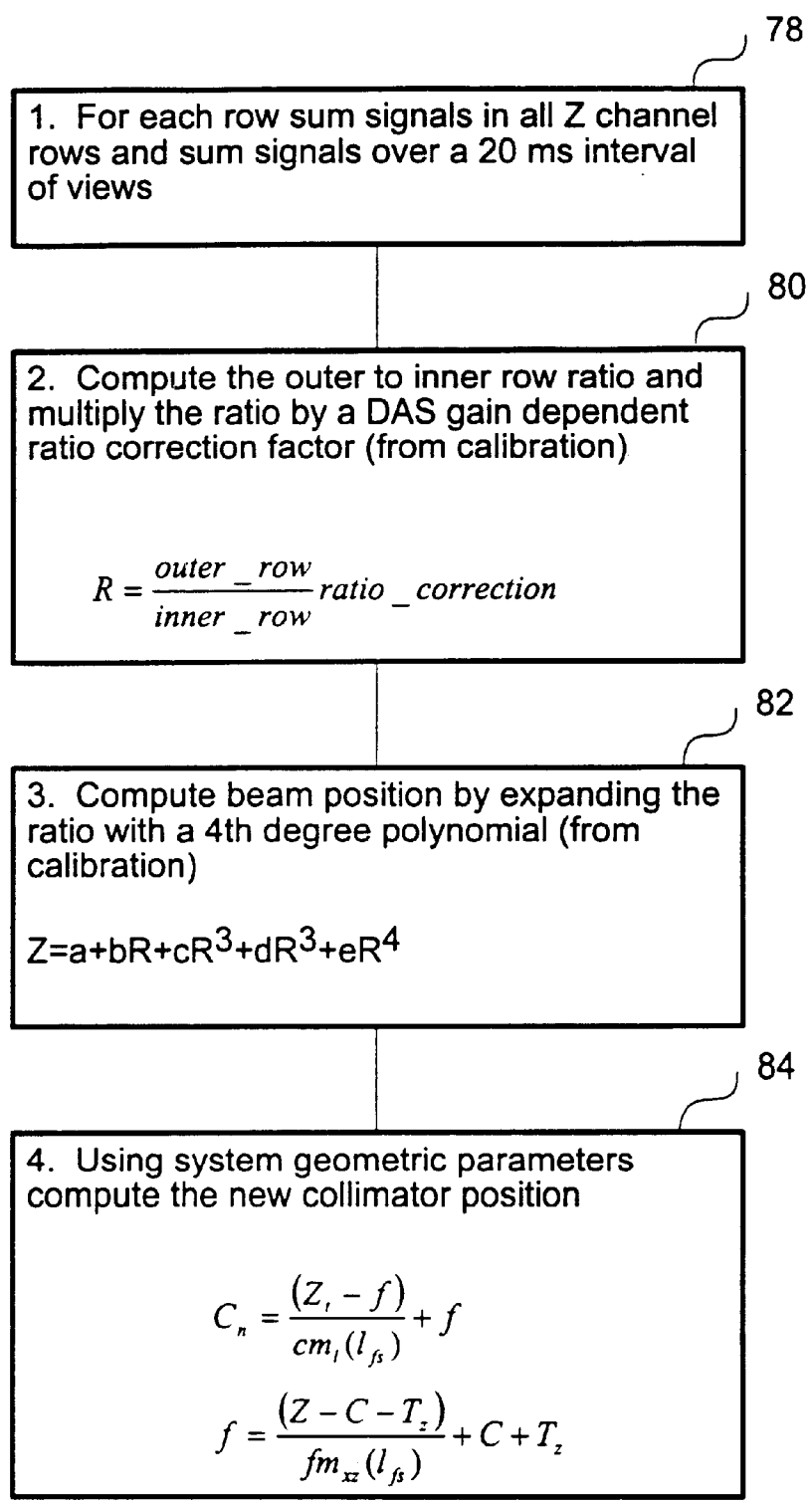
FIG. 4 is a flow diagram an embodiment of a z-axis tracking loop of the present invention.

As shown in FIG. 4, one embodiment of a closed-loop method for positioning beam 16 comprises comparing signals representative of X-ray intensity received from different rows of detector elements and positioning an X-ray beam in accordance with results of the comparison. In one embodiment, signals representative of X-ray intensity from detector rows 62, 64, 66 and 68 are summed 78 to obtain row sums. The summation is over views taken in a 20-millisecond interval. For example, after the analog signals are converted to digital format, hardware circuitry (not shown) is DAS 32 performs offset correction and determines row sums from signals received from outer row 62 and from inner row 64. A corrected ratio R is determined 80 by determining a ratio of a sum of signals received from outer row 62 to a sum of signals received from inner row 64 and multiplying the ratio by a ratio correction factor. The ratio correction factor, determined from imaging system 10 calibration, accounts for different relative DAS gains between outer row 62 and inner row 64.

Beam position Z(R) then is determined 82, in millimeters relative to a centerline. Beam position Z is obtained by applying a predetermined beam position transfer function to the corrected ratio to calculate the X-ray beam position. The beam position transfer function Z(R) is represented, for example, by a fourth-degree polynomial having predetermined coefficients:

$$Z(R) = a + bR + cR^2 + dR^3 + eR^4 \qquad \text{Eq. 1}$$

Beam position transfer function Z(R) and its limits are specified at imaging system 10 calibration.

A new collimator position is then determined 84. A focal spot position f is determined 84 from beam position Z, current collimator position C and other system 10 geometric parameters in accordance with:

$$f = \frac{(Z - C - T_z)}{fm_{xz}(l_{fs})} + C + T_z \qquad \text{Eq. 2}$$

where $T_z$ represents a current taper of cam 74, $fm_{xz}$ represents a focal spot magnification factor at rows 62 and 64 and is a function of focal spot size, and $I_{fs}$ represents focal spot 50 length. A new position for collimator 52 then is determined 84 for a detector element 20 positioned toward isocenter 24. Collimator 52 is repositioned where an edge (not shown) of collimator 52 would meet a line between focal spot position f and a target beam position $Z_t$ which has been specified at imaging system 10 calibration. New collimator position $C_n$ thus is determined in accordance with:

$$C_n = \frac{(Z_t - f)}{cm_l(l_{fs})} + f \qquad \text{Eq. 3}$$

where $cm_l$ represents a current collimator magnification factor at detector element 20 positioned toward isocenter 24 and is a function of focal spot size, and $I_{fx}$ represents focal spot 50 length.

In one embodiment, steps 78, 80, 82 and 84 are performed independently for each side of collimator 52 at intervals to continuously obtain new positions for each side of collimator 52. These intervals are, in one embodiment, 20 milliseconds, to sample the X-ray beam 16 position 25 times during a 0.5 second scan to minimize control loop lag error. However, in other embodiments, the interval is between 5 milliseconds and 50 milliseconds. In still other embodiments, the interval is between a minimum value sufficient to avoid effects of quantum noise and high frequency variation (such as due to X-ray tube anode movement at a run frequency between 50 Hz and 160 Hz) and a maximum constrained by a slew rate of the sag curve. Sampling the changing sag curve frequently avoids excessive positioning error. Sampling the changing sag curve frequently avoids excessive positioning error. (Sag is a periodic movement of X-ray beam 16 resulting from gravity and from centrifugal forces acting on mechanical structure during a rotation of gantry 12.)

During patient scanning, z-position detectors 62, 64, 66 or 68 may become blocked by patient clothing, blankets, or other objects. After blockage of a z-position detector 62, 64, 66 or 68 has been detected, or when X-ray source 14 first turns on, the loop sample interval is adjusted downward. In one embodiment, the loop sample interval is adjusted downward to 5 milliseconds. After 4 milliseconds of stabilization, the position of the beam is measured and collimator positioning is started to further minimize initial position errors.

During a blockage, loop operation is suspended. To determine if any z-position detectors are blocked, a signal from a last data detector element 90 adjacent a z-position detector 62, 64, 66 or 68 is compared to an expected signal Sx. Z-position detector blockage is assumed, in one embodiment, if a last data detector element 20 signal is less than 0.9 times expected signal Sx. In other embodiments, detector blockage is assumed when a last data detector element 20 signal is less than a value between 0.95 and 0.5 times expected signal Sx. (It is desirable to make this value as large in magnitude as possible to identify patient blockage as quickly as possible, thereby avoiding mis-positioning of X-ray beam 16 due to corrupted Z-measurement data. A maximum of 0.95 is used in one embodiment because it is known that X-ray scatter blockage from large patients 22, for example, can reduce a signal to 0.95 times the expected value.) During a blockage, collimator positioning is suspended. However, position measurement continues at an interval that is decreased from 20 to 5 milliseconds. The decreased measurement interval allows imaging system 10 to more quickly detect an end of the blockage and to presume closed-loop positioning.

Expected signal Sx is written as:

$$Sx = gmA * dsf * t * g \qquad \text{Eq. 4}$$

Where gmA is a generator current mA signal proportional to an X-ray source 14 energizing current, dsf is a scale factor determined at system 10 calibration, t is a DAS sample time period, and g is a gain factor. Gain factor g allows expected signal Sx to be adjusted according to a gain value used for scanning. In one embodiment, this gain value is selectable from a plurality of gain values available in system 10.

In one embodiment, closed loop tracking is suspended when signal corruption is detected. Signal corruption is detected, for example, by determining an actual focal spot length from a beam position and a collimator position, and comparing the actual focal spot length to a nominal focal spot length. When a difference of, for example, more than 0.1 millimeter is detected between the actual focal spot length and the nominal spot length, corruption is assumed to exist and collimator positioning is suspended. (In other embodiments, a difference threshold for assuming corruption is as small as 0.05 millimeter or as large as about 0.6 millimeter. In still other embodiments, a value is selected between a lower limit set by higher probabilities of false activation due to noise, X-ray scatter and/or momentary beam position disturbances and an upper limit that still provides some of the advantages of tracking.) However, beam position measurement continues at a decreased interval, as when a blockage is detected. Such corruption may occur, for example, for a short time just prior to or just following detection of a patient blockage. If the corruption persists, for example, over 90° of rotation of gantry 12 without detecting a patient blockage, a malfunction of the tracking system requiring servicing has likely occurred. In such an event, a scan is immediately aborted to avoid patient dose and collection of non-diagnostic quality images. In other embodiments, a limit is set from as little at 45° to as much as 360° of a rotation of gantry 12. In other embodiments, a limit is set between a value at which a false alarm rate due to scatter and/or an occasional exceptionally long partial patient 22 blockage is acceptable and an upper limit representing a design choice as to how long compromised operation (high dose and/or non-diagnostic quality images) can be tolerated before terminating a scan.

After system 10 has been switched off, position of focal spot 50 changes as source 14 cools over time. In one embodiment, before system 10 is switched on again, an initial focal spot position is approximated from information obtained when a focal spot was last measured. An approximation of a linear function is used to model focal spot position change during cooling in one embodiment, and in another embodiment, the linear function is a 97 nanometer per second linear function. Because position change with cooling is an exponential function, the linear approximation is clamped at 0.15 millimeters. This clamping corresponds to approximately 20% of a cooling change in system 10 when fully cold, where a linear approximation to the exponential function suffices. A fully cold position requires 8 to 12 hours without patient scanning, and a tube warm up prior to patient scanning is normally requested if the tube has been off more than 1 hour. Therefore, a fully cold position, although possible, is not likely during normal patient scanning. During tube warm up a current measured position of the focal spot is established again for initial positioning of the collimator.

Figure 5:
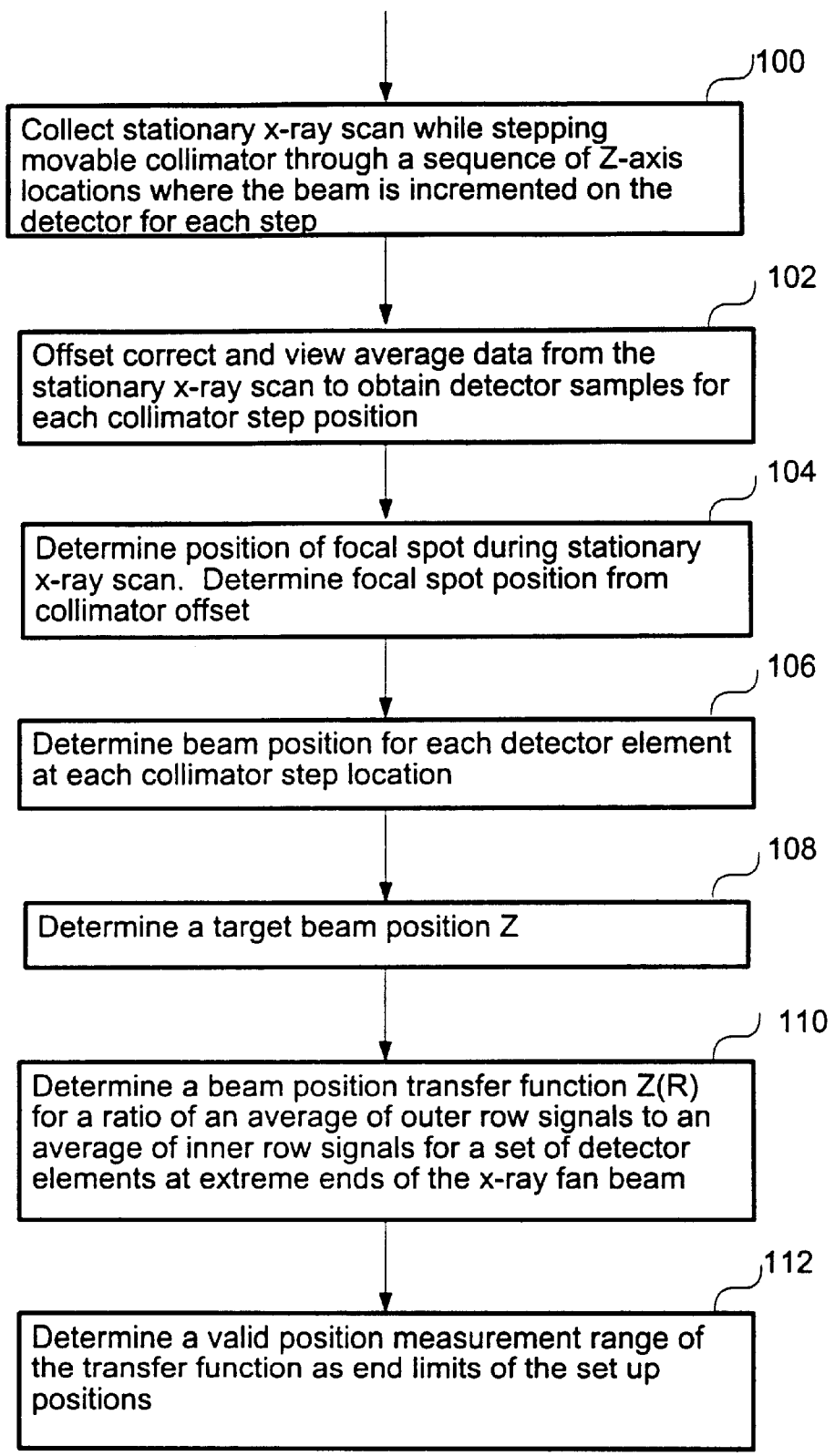
FIG. 5 is a flow diagram of a method for calibrating tracking loop parameters.

Several tracking loop parameters described herein, specifically, beam position transfer function Z(R) and its limits and target beam position $Z_t$, are determined at system 10 calibration. FIG. 5 illustrates one embodiment of a method for calibrating tracking loop parameters. In this embodiment, data from a stationary sweep scan is collected 100 while collimator 52 is stepped through a sequence of z-axis positions. Beam 16 is incremented 0.3 millimeters on detector array 18 exposure surface for each collimator 52 step position. The sweep scan data is offset-corrected and view averaged 102 to obtain a set of detector samples for each collimator 52 step position. A position of the focal spot is then determined 104. A collimator 52 z-axis position offset from detector array centerline $D_0$ is determined 104, as the point where outer rows 62 and 68 receive signals of half-maximum intensity at full detector element 20 width. Position of focal spot 50 during sweep scan then is determined 104 from collimator 52 z-axis offset and nominal system 10 geometric parameters.

A beam 16 position is determined 106 for each detector element 20 at each collimator 52 step position. Beam 16 positions are determined from sweep scan focal spot 50 position, nominal length of focal spot 50, and nominal system 10 geometry.

Target beam position $Z_t$ then is determined 108 for detector element 20 positioned toward isocenter 24. When beam 16 is directed at target beam position $Z_t$, beam 16 is sufficiently close to detector array 18 edge 92 to prevent imaging artifacts but is far enough away to minimize patient dosage. To determine target beam position $Z_t$, ratios of detector samples for successive collimator 52 step positions are utilized to determine a detector differential error. A reconstruction error sensitivity function w(i) then is applied to weight the detector differential error. Reconstruction error sensitivity function w(i) is related to the percent positive contribution of a detector element 20 as a function of its radial distance from isocenter 24. Function w(i), in one embodiment, is computed from nominal system geometry. In another embodiment, w(i) is empirically determined. For example, the following equations describe an empirical determination of w(i):

$$b(i)=0.018, \ 0 \leq i \leq 5$$

$$b(i)=0.035+0.00075x(i-5), \ 5\leq i\leq 213$$

$$b(i)=0.414+0.00365x(i-213), \ 214\leq i\leq n \quad \text{Eq. 5}$$

where i represents detector element position from isocenter 24 and b(i) represents an artifact threshold, i.e. a percent differential error, for a double detector element 20 error. Reconstruction error sensitivity function w(i) then is determined in accordance with:

$$w(i)=0.18/b(i) \quad \text{Eq. 6}$$

A collimator 52 step position SP is determined for which the weighted detector differential error exceeds a limit L empirically known to produce image artifacts, for example, 0.04 percent. Target beam position Z, then is set for the isocenter detector element at a distance just preceding SP by an amount exceeding applicable tracking loop positioning error.

Beam position transfer function Z(R) then is determined 110 for a ratio R of an average of outer row 62 to inner row 64 signals for a set of detector elements at an extreme end of X-ray fan beam 16. Beam 16 positions, determined 106 for each collimator 52 step position, are fitted to the ratio for each collimator 52 step position with a fourth-degree polynomial, for example, in accordance with:

$$Z(R)=a+bR+cR^2+dR^3+eR^4 \quad \text{Eq. 7}$$

over a suitable ratio range between a maximum and minimum for the sequence of steps.

A valid position measurement range for Z(R) is determined 112 as between end limits of the set of collimator 52 step positions for which an error between a beam 16 position determined by Z and an actual beam 16 position is less than a predetermined limit, for example, 0.2 millimeters. In other embodiments, the predetermined limit is between 0.1 millimeters to 0.6 millimeters. In still other embodiments, the predetermined limit is set at a value between a lower limit just above a value at which a range of beam 16 position that can be precisely measured is too limited, and just below a lower limit that is deemed to create tracking errors so large as to unacceptably compromise the benefits of tracking.

The above described tracking loop senses the signal ratio between detector rows and moves system collimation to maintain the X-ray beam very close to the imaging system detector array edge during patient scanning. As a result, patient X-ray dosage is reduced 20 to 40 percent without sacrificing image quality.

Other functions can be utilized in place of beam position transfer function Z(R) and also in place of reconstruction error sensitivity function w(i). In some embodiments, the methods described herein are implemented by software, firmware, or by a combination thereof controlling either computer 36, image reconstructor 34, or both. Also, additional z-detector rows can be provided. In such an embodiment, various combinations of z-detector row signals can be used as the inner and outer row signals, thereby becoming identified as such, or a different and/or more elaborate transfer function can be used to determine a beam position.

B. Second Embodiment

This second embodiment, referred to as a dual Z-position embodiment, describes several embodiments of a system that tracks relative beam-detector position at two separate fan beam positions and adjusts beam position as a function thereof. According to this dual Z-position embodiment all of the description above is applied to separate first and second detector element subsets within the same rows or array detectors, a first element subset located at one end of the array and a second subset located at the other end of the array.

To this end, referring again to FIG. 2, as well known in the CT art, detector array 18 typically includes separate detector modules. For the purpose of explaining the dual Z-position embodiment it will be assumed that each component 20 in FIG. 2 is a separate module with end modules identified as ML and MH where the L and H refer to low and high array ends, respectively. Referring also to FIG. 3, for the purpose of explaining the dual Z-position embodiment it will be assumed that the illustrated detector segment (e.g., 18 that was referred to above as the entire detector array) comprises end module ML including four columns and twelve rows of detector elements. End module MH is essentially identical to end module ML and therefore only module ML will be described in some detail.

Referring still to FIGS. 2 and 3, numerals 62, 64, 66 and 68 identify four of the twelve detector rows in module ML. When a plurality of modules 20 are arranged to form array 18 (see FIG. 2), the detector rows in each module line up and the columns are aligned with the Z axis 24. Thus, where each module includes twelve rows as does module ML, the detector array 18 includes twelve array rows, each array row including four detector elements from each module.

As with the single Z-position embodiment described above, in the case of the dual Z-position embodiment a collimator 52 including cams 74 and 76 is used to collimate a beam 16 emanating from a source 50. The resulting beam includes an umbra 70 and a penumbra 72 outside the umbra 70.

According to the dual Z-position embodiment, instead of using the beam position relative to an end of the detector array to adjust collimator cams, the position of a central isocentric fan beam relative to the array is used to control the collimator cams. To this end, Eq. 1 above is applied to each of the end modules ML and MH to determine the beam positions ZL and ZH, respectively, in millimeters relative to the centerline for the particular beam edge and corresponding cam. Thereafter, for each cam 74 and 76, Eq. 2 is solved twice, once using position ZL and a second time using position ZH, to generate first and second focal spot positions fL and fH, respectively. Specifically, the focal spot equations are:

$$fL = \frac{(ZL - C - T_z)}{fm_{zz}(l_{fs})} + C + T_z; \text{ and} \qquad \text{Eq. 8}$$

$$fH = \frac{(ZH - C - T_z)}{fm_{zz}(l_{fs})} + C + T_z$$

Next, for each cam 74 and 76, Eq. 3 is solved twice, once using first focal spot position fL and a second time using position fH, to generate first and second intermediate cam position commands CL and CH, respectively. Specifically, the intermediate position command equations are:

$$CL = \frac{(Z_t - fL)}{cm_i(l_{fs})} + fL; \text{ and} \qquad \text{Eq. 9}$$

$$CH = \frac{(Z_t - fH)}{cm_i(l_{fs})} + fH$$

Next, for each cam the intermediate cam position commands CH and CL are combined to generate a final cam command Cf according to the following equation:

$$Cf = (CH + CL)/2 \qquad \text{Eq. 10}$$

After the cam commands are determined in this manner the cam positions are modified as described above so that the isocenter beam (i.e., the central ray of beam 16 in FIG. 3) is properly positioned on the detector. While dynamic skew still occurs along Z at lateral fan angles, artifact sensitivity is, nevertheless, significantly decreased.

If any portion of either of modules ML or MH that is required for determining the Z-positions of beam 16 is occluded (i.e., by a portion of a patient's body or the like), then another method must be provided to identify the final cam command C corresponding to the isocentral beam. To this end one embodiment of the present invention includes sensing when required module detectors are blocked and, when the required detectors are blocked, determining the cam command by solving the following equations:

If ML corresponding to a cam is blocked, then:

$$C = CU - CHU + CHc \qquad \text{Eq. 11}$$

If MH corresponding to a cam is blocked, then:

$$C = CU - CLU + CLc \qquad \text{Eq. 12}$$

where "U" designates the last unblocked cam command and "c" designates the currently computed cam command.

Thus, tracking continues by indexing the cam command relative to the last known mean position even when one of the ML or MH modules is blocked. The net result is that errors during blockage are minimized as the total time of blockage is significantly reduced (i.e., the total time during which both end modules ML and MH are blocked will be much smaller in duration than the time during which a single one of end modules ML and MH is blocked.

Figure 6:
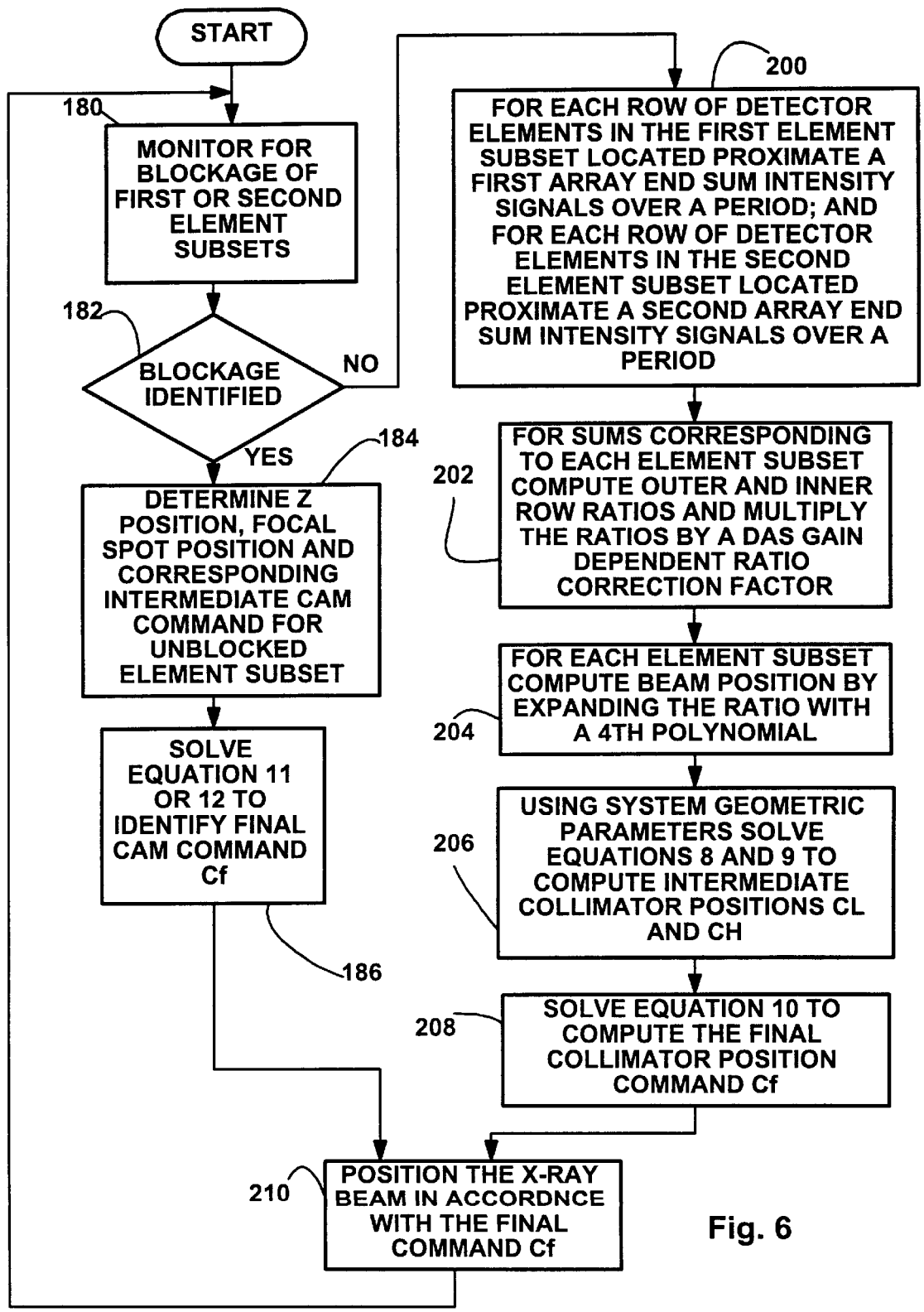
FIG. 6 is a flow chart illustrating one method according to the present invention.

Referring now to FIG. 6, therein is illustrated one embodiment of the dual Z-position method according to the present invention. To this end, referring also to FIGS. 1, 2 and 3, with source 14 turned on so that beam 16 is directed at detector 18 and, specifically, portions of beam are directed at end modules ML and MH, at process block 180 a processor within computer 36 monitors for blockage of first or second element subsets corresponding to modules ML and/or MH. At decision block 182, assuming that neither of the first or second element subsets is blocked, control passes to block 200.

At block 200, the processor sums intensity signals over a period for each row of detector elements in the first element subset. Similarly, the processor sums the intensity signals over the same period for each row of detector elements in the second element subset. Continuing, at block 202, for sums corresponding to each of the first and second element subsets, the processor computes outer and inner row ratios and multiplies the ratios by a DAS gain dependent ratio correction factor. Next, at block 202, for each of the first and second element subsets, the processor computes beam position by expanding the corresponding ratio with a fourth polynomial (e.g., see Eq. 1 above).

At process block 206, the processor uses system geometric parameters and solves Eqs. 8 and 9 above to compute intermediate collimator positions CL and CH. Next, at process block 208, the processor solves Eq. 10 above to compute the final collimator position command Cf. Thereafter control passes to block 210 where the processor causes the beam limiter (i.e., the collimator) to position the x-ray beam in accordance with the final command Cf. Control then passes back up to block 180 where the process starts over again.

Referring still to FIG. 6, at decision block 182 if either the first or second element subsets are blocked, control passes to block 184. At block 184, the processor determines the Z-position, focal spot position and corresponding intermediate cam command for the unblocked element subset. For example, referring to FIGS. 2 and 6, if the first element subset corresponding to module ML is blocked, at block 184 the processor determines the Z-position, focal spot position, and corresponding intermediate cam command CH for the second unblocked element subset that corresponds to module MH. Continuing, at block 186, the processor solves Eq. 11 or Eq. 12 to identify the final cam command Cf. Once again, at block 210, the processor causes the limiter or collimator to position the x-ray beam 16 in accordance with the final command Cf prior to control looping back to block 180 to repeat the process again.

While not explained here again in detail with respect to the dual Z-position system, it should be appreciated that all of the features described above with respect to the single Z-position system are applicable to the dual system including the loop sample interval adjustment, corruption detection and resulting affirmative action (i.e., stoppage of irradiation upon excessive corruption, etc.), and calibration methods.

It should be understood that the methods and apparatuses described above are only exemplary and do not limit the scope of the invention, and that various modifications could be made by those skilled in the art that would fall under the scope of the invention. For example, while the first and second element subsets are described above as including all elements within specific rows of end modules ML and MH, clearly the invention contemplates other embodiments where the first and second subsets include other element sets including partial rows within the end modules or rows that extend beyond the end modules or rows from other modules proximate the end modules.

To apprise the public of the scope of this invention, the following claims are made:

What is claimed is:

1. A method for positioning an X-ray beam on a multi-slice detector array of an imaging system, the detector array having rows of detector elements that extend between first and second array ends and configured to detect X-rays in slices along a Z-axis, the method comprising the steps of:

comparing data signals representative of X-ray intensities received from different rows of detector elements within a first element subset where the first element subset is located proximate the first array end;

comparing data signals representative of X-ray intensities received from different rows of detector elements within a second element subset where the second element subset is located proximate the second array end; and positioning the X-ray beam in accordance with a result of the comparisons.

2. The method of claim 1 wherein the comparing steps include comparing signals where the first and second element subsets are at the opposite ends of the array.

3. The method of claim 1 wherein the step of comparing signals from the first element subset includes determining a ratio of a sum of signals representative of X-ray intensity received from different rows of detector elements within the first subset over a time interval, the step of comparing signals from the second element subset includes determining a ratio of a sum of signals representative of X-ray intensity received from different rows of detector elements within the second subset over the time interval and wherein the step of positioning comprises the step of positioning the X-ray beam in accordance with the determined ratios.

4. The method of claim 3 wherein the step of determining a ratio within the first subset includes determining a sum of signals received from an inner row of within the first subset over a time interval, and determining a sum of signals received from an outer row within the first subset over the time interval and the step of determining a ratio within the second subset includes determining a sum of signals received from an inner row of within the second subset over a time interval, and determining a sum of signals received from an outer row within the second subset over the time interval.

5. The method of claim 4 wherein the X-ray beam is a fan beam, and wherein the step of positioning comprises applying a ratio correction factor to the determined ratios to obtain first and second corrected ratios corresponding to the first and second array ends, and identifying first and second X-ray beam positions ZL and ZH as a function of the first and second corrected ratios.

6. The method of claim 5 wherein the step of identifying first and second X-ray beam positions ZL and ZH as a function of the first and second corrected ratios comprises applying a beam position transfer function to each of the first and second corrected ratios to identify the first and second X-ray beam positions.

7. The method of claim 6 wherein said imaging system includes a collimator configured to collimate and position the X-ray beam, the collimator having at least one cam having a taper, and said method further comprising the step of, for the first and second X-ray beam positions, determining first and second focal spot positions fL and fH, respectively, by solving the following equations:

$$fL = \frac{(ZL - C - T_z)}{fm_{zz}(l_{fs})} + C + T_z; \text{ and}$$

$$fH = \frac{(ZH - C - T_z)}{fm_{zz}(l_{fs})} + C + T_z$$

where C is a current collimator position, $T_z$ is a current cam taper, $fm_{zz}$ is a focal spot magnification factor and $l_{fs}$ is a focal spot length.

8. The method of claim 7 further comprising the step of, for the first and second focal spot positions fL and fH, determining first and second intermediate collimator positions CL and CH, respectively, by solving the following equations:

$$CL = \frac{(Z_t - fL)}{cm_i(l_{fs})} + fL; \text{ and}$$

$$CH = \frac{(Z_t - fH)}{cm_i(l_{fs})} + fH$$

where $Z_t$ is a target beam position at which to maintain the X-ray beam, $cm_i$ is a collimator magnification factor, and $l_{fs}$ is a focal spot length.

9. The method of claim 8 further including the step of combining the first and second intermediate collimator positions CL and CH to identify a final collimator position command Cf by solving the following equation:

$$Cf=(CH+CL)/2.$$

10. Claim 9 further comprising the step of positioning the outer row of the detector array substantially within a penumbra of the X-ray beam and the inner row of the detector array substantially within an umbra of the X-ray beam.

11. The method of claim 3 wherein said step of comparing data signals representative of X-ray intensity received from the first and second element subsets is performed a plurality of times, the method further comprising the steps of monitoring for blockage of either the first or second element subset detectors and, where blockage is identified, if detector elements from the first element subset are blocked, solving the following equations to identify the final collimator position command Cf:

$$C=CU-CHU+CHc; \text{ and}$$

if detector elements from the second element subset are blocked, solving the following equations to identify the final collimator position command Cf:

$$C=CU-CLU+CLc$$

where U designates the last unblocked cam command and c designates the currently computed cam command.

12. An positioning system for use with an imaging system including an X-ray source that generates an X-ray beam and a multi-slice detector array having rows of detector elements that extend between first and second array ends and configured to detect X-rays in slices along a Z-axis, the positioning system for positioning the X-ray beam on the array and comprising:

a beam limiter for defining the beam; and a processor running a pulse sequencing program to perform the steps of:

comparing data signals representative of X-ray intensities received from different rows of detector elements within a first element subset where the first element subset is located proximate the first array end;

comparing data signals representative of X-ray intensities received from different rows of detector elements within a second element subset where the second element subset is located proximate the second array end; and causing the limiter to position the X-ray beam in accordance with a result of the comparisons.

13. The positioning system of claim 12 wherein the program causes the processor to perform the comparing steps by comparing signals where the first and second element subsets are at the opposite ends of the array.

14. The positioning system of claim 12 wherein the program causes the processor to perform the step of comparing signals from the first element subset by determining a ratio of a sum of signals representative of X-ray intensity received from different rows of detector elements within the first subset over a time interval and to perform the step of comparing signals from the second element subset by determining a ratio of a sum of signals representative of X-ray intensity received from different rows of detector elements within the second subset over the time interval and wherein the step of positioning comprises the step of positioning the X-ray beam in accordance with the determined ratios.

15. The positioning system of claim 14 wherein the program causes the processor to perform the step of determining a ratio within the first subset by determining a sum of signals received from an inner row of within the first subset over a time interval, and determining a sum of signals received from an outer row within the first subset over the time interval and the program causes the processor to perform the step of determining a ratio within the second subset by determining a sum of signals received from an inner row of within the second subset over a time interval, and determining a sum of signals received from an outer row within the second subset over the time interval.

16. The positioning system of claim 15 wherein the X-ray beam is a fan beam, and wherein the program causes the processor to perform the step of positioning by applying a ratio correction factor to the determined ratios to obtain first and second corrected ratios corresponding to the first and second array ends, and identifying first and second X-ray beam positions ZL and ZH as a function of the first and second corrected ratios.

17. The positioning system of claim 16 wherein the program causes the processor to perform the step of identifying first and second X-ray beam positions ZL and ZH as a function of the first and second corrected ratios by applying a beam position transfer function to each of the first and second corrected ratios to identify the first and second X-ray beam positions.

18. The positioning system of claim 17 wherein the limiter includes a collimator configured to collimate and position the X-ray beam, the collimator having at least one cam having a taper, and said processor further running the pulse sequencing program to perform the steps of, for the first and second X-ray beam positions, determining first and second focal spot positions fL and fH, respectively, by solving the following equations:

$$fL = \frac{(ZL - C - T_z)}{fm_{zz}(l_{fs})} + C + T_z; \text{ and}$$

-continued
$$fH = \frac{(ZH - C - T_z)}{fm_{zz}(l_{fs})} + C + T_z$$

where C is a current collimator position, $T_z$ is a current cam taper, $fm_{zz}$ is a focal spot magnification factor and $I_{fs}$ is a focal spot length.

19. The positioning system of claim 18 wherein the processor runs the pulse sequencing program to further perform the steps of, for the first and second focal spot positions fL and fH, determining first and second intermediate collimator positions CL and CH, respectively, by solving the following equations:

$$CL = \frac{(Z_t - fL)}{cm_i(l_{fs})} + fL; \text{ and}$$

$$CH = \frac{(Z_t - fH)}{cm_i(l_{fs})} + fH$$

where $Z_t$ is a target beam position at which to maintain the X-ray beam, $cm_i$ is a collimator magnification factor, and $I_{fs}$ is a focal spot length.

20. The positioning system of claim 19 wherein the processor runs the pulse sequencing program to further perform the steps of combining the first and second intermediate collimator positions CL and CH to identify a final collimator position command Cf by solving the following equation:

$$Cf=(CH+CL)/2.$$

21. The positioning system of claim 20 wherein the processor runs the pulse sequencing program to further perform the step of positioning the outer row of the detector array substantially within a penumbra of the X-ray beam and the inner row of the detector array substantially within an umbra of the X-ray beam.

22. The positioning system of claim 14 wherein the pulse sequencing program causes the processor to perform the step of comparing data signals representative of X-ray intensity received from the first and second element subsets a plurality of times, the processor running the pulse sequencing program to further perform the steps of monitoring for blockage of either the first or second element subset detectors and, where blockage is identified, if detector elements from the first element subset are blocked, solving the following equations to identify the final collimator position command Cf:

$$C=CU-CHU+CHc; \text{ and}$$

if detector elements from the second element subset are blocked, solving the following equations to identify the final collimator position command Cf:

$$C=CU-CLU+CLc$$

where U designates the last unblocked cam command and c designates the currently computed cam command.

* * * * *